US005192815A

United States Patent [19]
Okada et al.

[11] Patent Number: 5,192,815
[45] Date of Patent: Mar. 9, 1993

[54] DENTAL RESTORATIVE MATERIAL
[75] Inventors: Koichi Okada; Ikuo Omura, both of Kurashiki, Japan
[73] Assignee: Kuraray Co., Ltd., Kurashiki, Japan
[21] Appl. No.: 430,331
[22] Filed: Nov. 2, 1989
[30] Foreign Application Priority Data
Nov. 11, 1988 [JP] Japan .................. 63-286404
[51] Int. Cl.$^5$ .......................... A61F 2/00; C08J 5/10; C08K 3/36; C08L 33/12
[52] U.S. Cl. .................................. 523/115; 523/116; 523/212; 523/213
[58] Field of Search ................ 523/116, 115, 212, 213

[56] References Cited
U.S. PATENT DOCUMENTS
4,302,381 11/1981 Omura et al. ................ 523/116
4,544,359 10/1985 Waknine ...................... 523/115
4,859,716 8/1989 Ibsen et al. .................... 523/116
4,872,936 10/1989 Engelbrecht ................ 523/116

Primary Examiner—Paul R. Michl
Assistant Examiner—U. K. Rajguru
Attorney, Agent, or Firm—Oblon, Spivak, McClelland, Maier & Neustadt

[57] ABSTRACT

Provided is a dental restorative material having high mechanical strength, abrasion resistance, hardness and excellent aesthetic appearance because it contains a large amount of an ultrafine filler having a particle size of 0.1 μm or less, and can hence be used for restoring molars as well as foreteeth. The dental restorative material comprises an inorganic filler with a size of 0.1 μm or less which is insoluble in water and surface-treated with a silane coupling agent represented by the following general formula:

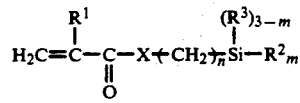

and a (meth)acrylate monomer composition containing at least 50% by weight based on the weight of the composition of at least one hydrophobic multifunctional (meth)acrylate represented by the following general formula:

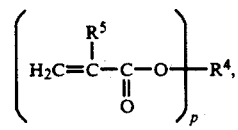

said surface-treated inorganic filler being incorporated in an amount of at least 100 parts by weight based on 100 parts by weight of said monomer composition.

10 Claims, No Drawings

DENTAL RESTORATIVE MATERIAL

BACKGROUND OF THE INVENTION

1. Field of the Invention

The present invention relates to dental restorative materials, and more specifically to novel dental restorative materials, which are polymer composites containing an ultrafine inorganic filler in a high density. The term "dental restorative material" as used herein means a composite material for dental use, which is generally called "dental composite resin" and is used as a material for filling and restoring teeth, material for making inlays, artificial crowns, artificial teeth, abutment construction materials, or the like.

2. Description of Prior Art

Recently, in the field of dental care, compositions containing an inorganic filler and a monomer, for example composite resins for dental use, have come into use. It is known that the inorganic fillers used in composite resins for dental use will exert various desirable effects for dental care when the range of their particle sizes are properly selected. More concretely, while granular fillers having a size of not more than 20 μm had been used in the past, finer fillers having a particle size of not more than 0.1 μm have more frequently been used these days, as shown in Japanese patent Application Laid-open Nos. 107189/1979, 82303/1982, 101409/1984 and 148109/1986 and Japanese patent Kohyo Nos. 500150/1982 and 501090/1986. The use of such fine fillers is said to contribute to an increase of mechanical strength, an improvement in polishability (gloss development when polished) and abrasion resistance, and this technology therefore is becoming of high importance in the dental fields.

The inorganic fillers used in composite resins for dental use are generally subjected to preliminary surface treatment. The surface treatment improves the wettability at the filler-monomer interface, improves the dispersibility of the filler in the composition and makes it possible to increase the filler content. As a result, composite resin moldings obtained by polymerization of the monomer have improved mechanical strength owing to good adhesion at the filler-resin interface. Known in the art as surface treating agents for such purposes are silane coupling agents, typically γ-methacryloyloxypropyltrimethoxysilane.

On the other hand, for the purpose of increasing adhesiveness of the organic-inorganic interface, the use of surface-treating silane couling agents other than the above-mentioned γ-methacryloyloxypropyltrimethoxysilane, having a longer alkylene group as a spacer between the methacryloyl group and the silyl group have to some extent been attempted; for example:

(1) Japanese patent publication No. 20871/1969 discloses a composition incorporating an inorganic filler surface-treated with a compound represented by the general formula

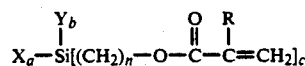

wherein R is a hydrogen atom or an alkyl group, X is a hydrolyzable group, y is a hydrocarbyl group, n is an integer of 7 to about 20, a is an integer of 1 to 3, b is an integer of 0 to 2, c is an integer of 1 to 3, and $a+b+c=4$.

However, the above composition differs from the dental restorative material of the present invention in that it utilizes monofunctional monomers as the principal monomer and that it uses only a coarse inorganic filler having a particle size of at least 0.2 μm. Furthermore, the specification has no description anticipating its application to dental care field.

(2) J. Jang, H. Ishida and E. P. Plueddeman, Proc. 41st Annual Conference, Reinforced Plastics/Composite Institute, The Society of the Plastics Industry, Session 2-C (1986) describes 11-methacryloyloxyundecyltrimethoxysilane. The reference discloses a polymer composite comprising a filler surface-treated with the above silane compound and a thermoplastic polyester resin. It however does not suggest a (meth)acrylate monomer as a matrix resin. Besides, the filler is surface-treated in a way not effective for the afore-mentioned silane coupling agent, being different from the way of the present invention. And further, the paper contains no description anticipating the use in dental field.

(3) Nishiyama, The Journal of the Japanese Society for Dental Materials and Devices, 3 (2), 284 to 294 (1984) shows 10-methacryloyloxydecyltrimethoxysilane. However, in this paper, while a glass plate is surface-treated with the compound and the state of the treated surface is compared with that treated with conventional γ-methacryloyloxypropyltrimethoxysilane, the surface-treating effect for fine inorganic fillers is not studied. Furthermore, although the paper states, as a general comment, that 10-methacryloyloxydecyltrimethoxysilane can be used as a surface-treating agent for fillers, it contains no concrete description at all on how to use the compound as a surface-treating agent for dental composite resins or on the make-up of composite resins.

(4) Japanese patent Application laid-open No. 159214/1988 discloses a surface-treating process of a particulate silica-based oxide complex, which comprises preliminarily treating said complex with an aliphatic amine and then treating the same with a silane coupling agent. κ-methacryloyloxydecyltrimethoxysilane is used as an example of such coupling agents. The technical point of this process is, since it uses the particulate complex having a high acidity, pKa of −3.0 to 3.0 on the surface sites, to treat with a silane coupling agent the particulate complex after its neutralization with an amine. Accordingly, there is no thought to set up an object of incorporating a large amount of a fine filler having a size of 0.1 μm or less into a monomer and to find out a silane coupling agent suited therefor. The afore-mentioned fine fillers, particularly those having a size of 0.1 μm or less, can be dispersed in a monomer in a far smaller amount than coarser fillers since the fine fillers cause a markedly large viscosity increase. As a result, the advantage of incorporating an ultrafine filler having a size of 0.1 μm or less, such as improvement in mechanical strength, abrasion resistance and polishability, has not fully been realized.

There has therefore been desired a technique of incorporating an ultrafine filler in a high density into a monomer, i.e. a resin matrix. Also has been desired a technique for improving adhesion of filler-matrix resin interface, which governs the durability of the dental restorative materials.

SUMMARY OF THE INVENTION

Accordingly, an object of the present invention is to provide a dental restorative material comprising an ultrafine filler having a size of 0.1 μm or less incorporated thereinto in a high density, which has high strength and high aesthetic appearance.

Another object of the present invention is to provide a dental retorative material with excellent durability, which can maintain high strength for a long period of time under wet conditions in the oral cavity where the material suffers repeated oclusal pressure.

The present inventors have investigated to solve the above-mentioned problems and found that the objects of providing high-density filling, high strength and high aesthetic appearance and improving durability can be achieved by the combined use of an ultrafine inorganic particulate filler with a size of 0.1 μm or less surface-treated with a silane coupling agent comprising (a) a (meth)acryloyl group and a linear alkylene group having at least 8 carbon atoms and (b) a hydrophobic multifunctional (meth)acrylate; wherein the term "(meth)acryloyl group" herein means either methacryloyl group or acryloyl group, and the term "(meth)acrylate" means either methacrylate or acrylate.

Thus, the present invention provides dental restorative materials comprising:

(a) an ultrafine inorganic filler with a size of 0.1 μm or less which is insoluble in water and surface-treated with a silane coupling agent represented by the following general formula (I) in an amount of at least 3% by weight based on the weight of the filler:

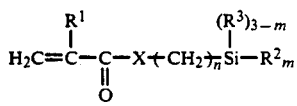

wherein $R^1$ is a hydrogen atom or a methyl group, $R^2$ is a hydrolyzable group, $R^3$ is a hydrocarbon group having 1 to 6 carbon atoms, X is an oxygen or sulfur atom, m is 2 or 3 and n is an integer of 8 to 20; and (b) a (meth)acrylate monomer composition containing at least 50% by weight based on the weight of the composition of at least one hydrophobic multifunctional (meth)acrylate represented by the following general formula (II):

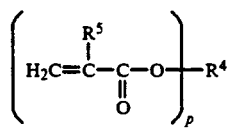

wherein $R^4$ is an organic group having 7 to 40 carbon atoms, being composed of 1 to 8 hydrocarbon groups having 2 to 40 carbon atoms, at least one of said hydrocarbon groups being a hydrocarbon group having at least 4 carbon atoms, the ratio of the number of total carbon atoms, x, contained in said hydrocarbon groups to the number of the hydrocarbon groups, y, contained in said organic group satisfying:

$x/y > 3$; $R^5$ is a hydrogen atom or a methyl group and p is an integer of 2 to 8;

wherein said surface-treated inorganic filler is incorporated in an amount of at least 100 parts by weight based on 100 parts by weight of the monomer composition.

The most characteristic feature of the present invention resides in the use of an ultrafine inorganic filler having a particle size of 0.1 μm or less surface-treated with a silane coupling agent represented by general formula (I) in combination with a hydrophobic multifunctional (meth)acrylate represented by general formula (II). The term "particle size" herein means an arithmetic mean of the major axis and the minor axis of the particle.

In the hydrophobic multifunctional (meth)acrylate, interactions among the particles of the ultrafine inorganic filler, which particles have been made highly hydrophobic by surface treatment with the silane coupling agent of formula (I), are extremely weakened so that the thickening (viscosity increasing) effect of the particles decreases and the filler can be incorporated in a high ratio. Moreover, since the (meth)acrylate is multifunctional, a highly crosslinked three-dimensional network structure develops between the filler and the resin matrix, thereby exhibiting high strength.

In the silane coupling agent (I), examples of $R^2$ include chlorine atom, alkoxy group, isocyanate group, acyloxy group and iminoxy group, among which particularly preferred are chlorine atom, alkoxy group and isocyanate group because of their high activity. Examples of the silane coupling agent (I) are as shown below.

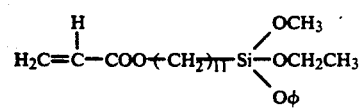

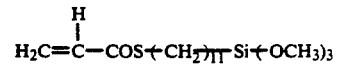

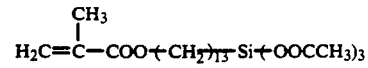

-continued

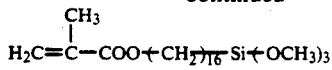

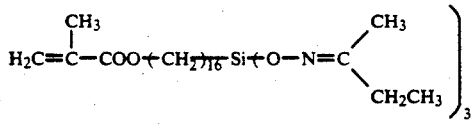

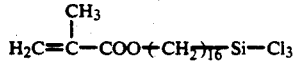

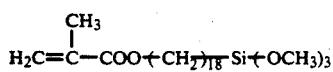

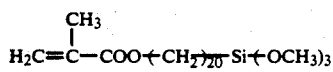

The inorganic filler with a particle size of 0.1 μm or less must be insoluble in water. The term "insoluble in water" as used herein is defined to be a saturation solubility in water at room temperature of not more than 0.1 wt %. Besides, since the filler should chemically bind the silane coupling agent (I), the filler should have as many hydroxyl groups as possible on the surface thereof.

When a crown is restored, it is preferred that the filler used develop the appearance of natural tooth, and be hence colorless transparent by itself and have a reflective index similar to that of the (meth)acrylate monomer described below.

Examples of the filler include silica-based minerals, such as kaolin, clay and mica; and silica-based ceramics or glasses containing oxide such as $Al_2O_3$, $B_2O_3$, $TiO_2$, $ZrO_2$, $BaO$, $La_2O_3$, $SrO_2$, $CaO$ and $P_2O_5$, in particular lanthanum glasses such as Shott GM31 684 ®, baruium glasses such as Shott GM27 884 ®, Shott 8253 ®, Ray-Sorb T-2000 ® and Ray-Sorb T-3000 ®, Strontium glasses such as Shott GM32-087 ® and Ray-Sorb T-4000 ®, bioglasses and the like. Also used preferably are hydroxyapatite, alumina, titanium oxide, zirconia, aluminum hydroxide and the like.

In the present invention, the above-mentioned fillers preferably have an acidity of surface site, pKa, of at least 3.3. Fillers with a pKa of less than 3.3 will accelerate discoloring of dental restorative materials containing them, which is not preferred. The acidity is measured according to the method described in K. Tanabe, T. Takeshita: Acid-Base Catalysis, p. 161 (1966), issued from Sangyo Tosho, Tokyo.

The inorganic fillers may have any form or shape without any limitation. Various forms, such as spherical, crushed, needle-like, whisker and platelet forms, may be used depending on the intended use of the composition.

The inorganic fillers can be surface-treated with silane coupling agents by known processes for surface-treating with silane coupling agents: e.g. a process which comprises adding a coupling agent (I) by spraying to an inorganic filler which is being agitated with blender; one which comprises dispersing an inorganic filler and a coupling agent (I) in an appropriate solvent and then distilling off the solvent; and one which comprises hydrolyzing in an aqueous solution a hydrolyzable group $R^2$ of a coupling agent (I) with acid catalyst into a silanol group, then permitting the thus hydrolyzed agent to react with an inorganic filler in the aqueous solution, and removing water. In any process, the reaction of the coupling agent with the filler completes by heating at 50° to 150° C.

Among the above-mentioned processes, preferred in the present invention is a process which comprises dispersing a silane coupling agent (I) and an inorganic filler in a hydrocarbon solvent and then heating the dispersion at a temperature of from 60° to 150° C. to effect the reaction of the surface of the inorganic filler with the silane coupling agent (I). Examples of the hydrocarbon solvent used in this process are hexane, heptane, decane, benzene, toluene, ethylbenzene, xylene, mesitylene, diethylbenzene, cyclohexane, chloroform, dichloroethane, trichloroethane, carbon tetrachloride and the like. The reaction proceeds more rapidly when the solvent has a boiling point of 150° C. or below and the dispersion is heated up to its boiling point. Further, since the reaction of the inorganic filler surface with a silane coupling agent is a condensation reaction such as dehydration, dealcohol and dehydration chloride reaction, the surface treatment can more effectively conducted by distilling off the reaction byproducts, e.g. water, alcohol or hydrogen chloride with the solvent from the reaction system. After the dispersion has been heated for a sufficient time to complete the reaction, the filler is recovered from the solvent by filtration, distilling off of the solvent under a reduced pressure, centrifugal separation, lyophilization or the like, and then dried to complete the entire process.

The amount of the silane coupling agent (I) used for the inorganic filler is determined such that the desired properties of the obtained dental restorative material will be highest, based on preliminary experiments. The amount should be at least 3% by weight based on the weight of the inorganic filler to be treated. If the amount is less than this, the filling density of the filler will decrease and hence the mechanical strength of the restorative material obtained will decrease, which are not preferred.

The monomer (b) used in the present invention is suitably selected depending on the intended use of the dental restorative material to prepare. It should copolymerize with the silane coupling agent (I) used for surface treatment, and, in particular, multifunctional (meth)acrylates of formula (II) are used. The term "multifunctional" as used herein means that the monomer has 2 to 8 (meth)acryloyloxy groups in the molecule thereof Further the term "hydrocarbon group" includes those substituted with halogen atoms for hydrogen atoms, and the term "organic group" means a hydrocarbon group or a group constituted by linking at least two hydrocarbon groups with at least one single bond unit or a composite bond unit comprising such single bond units, the single bond unit being selected from the following group

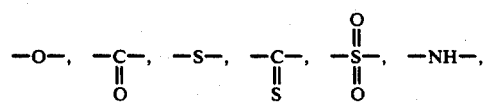

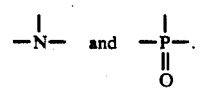

There are several restrictions on the molecular structure of the multifunctional (meth)acrylate used in the invention for the purpose of achieving high-density filling. That is, $R^4$ in formula (II) should be a hydrophobic, comparatively large organic group having 7 to 40 carbon atoms. The organic group may either be a single hydrocarbon group or assume a composite structure comprising a plurality of hydrocarbon groups having 2 to 38 carbon atoms linked with each other through the above-mentioned bond units. In the latter case, at least one of the hydrocarbon groups should be a hydrophobic group having at least 4 carbon atoms. It is necessary that the number of the afore-mentioned bond units do not exceed an upper limit relative to the number of total carbon atoms since these bond units exhibit by themselves a function of decreasing the hydrophobicity of the organic group and hence preventing a high-density filling of the filler. Thus, the ratio of the number of total carbon atoms in $R^4$, x, to the number of the hydrocarbon groups in $R^4$, y, should satisfy the formula $x/y > 3$. If $x/y \leq 3$, the thickening effect will be large, thereby rendering the high-density filling of the filler difficult to achieve. Furthermore, $R^4$ should not contain a highly polar functional group such as hydroxyl group, carboxyl group, amino group, phosphoric acid group (this means

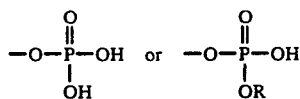

wherein R is an organic group) or thiol group since such polar group significantly decrease the hydrophobicity of the organic group $R^4$.

Examples of the multifunctional (meth)acrylate represented by formula (II) are as follows.

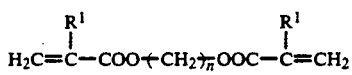

wherein n is an integer of 7 to 20 and $R^1$ is a methyl group or a hydrogen atom,

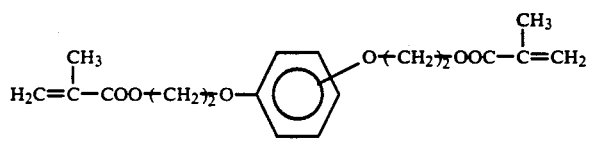

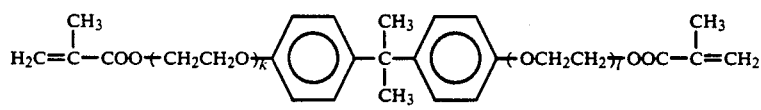

wherein k and l are integers satisfying $k + l = 2$ to 11,

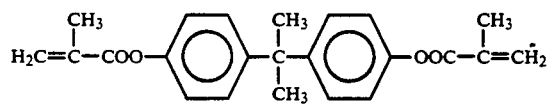

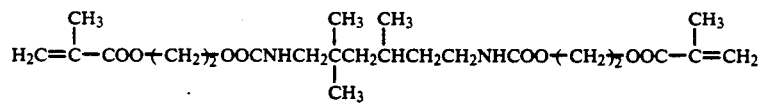

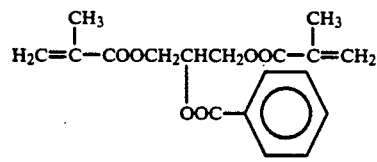

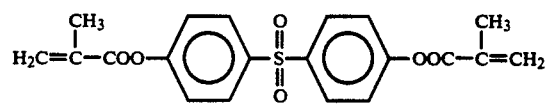

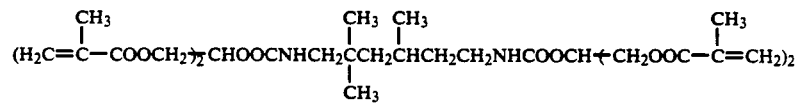

-continued

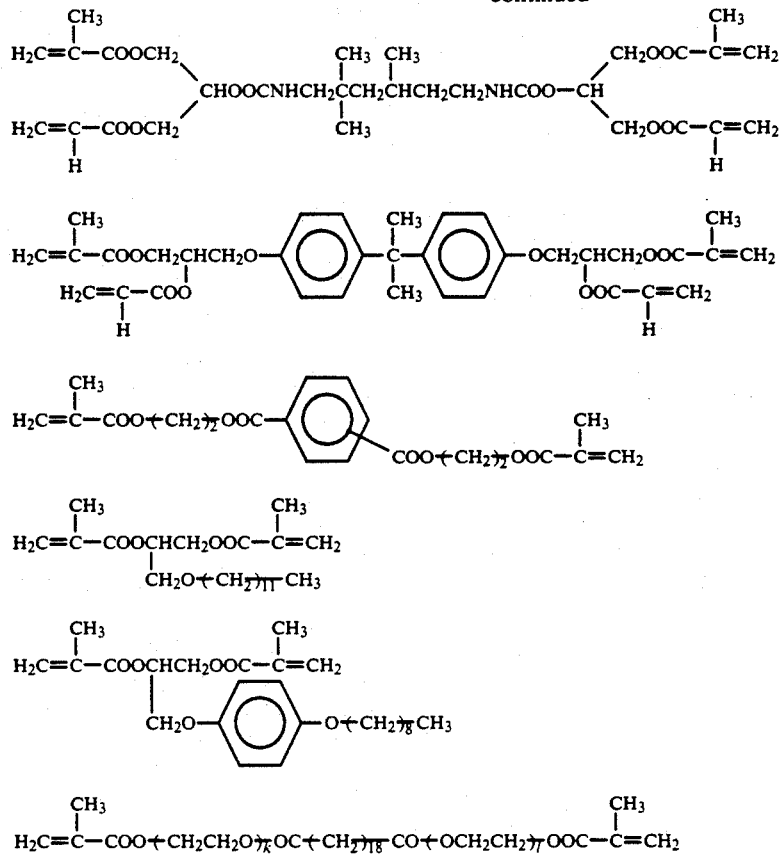

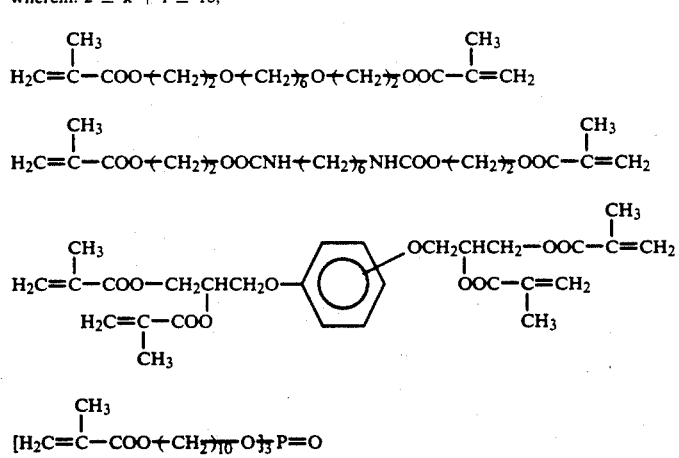

wherein: $2 \leq k + l \leq 10$,

According to the aforementioned reasons, i.e. the high-density filling of the filler and crosslinked structure of the resin matrix, the multifunctional (meth)acrylate monomer is incorporated into a monomer composition in an amount of at least 50% by weight, preferably at least 65% by weight of the monomer composition.

While in the present invention a multifunctional (meth)acrylate which is not represented by formula (II) can also be used, its incorporation ratio must be in a range not exceeding 50% by weight based on the weight of total monomer composition (b), preferably in a range not exceeding 35% by weight on the same basis. Examples of such multifunctional (meth)acrylate are as follows.

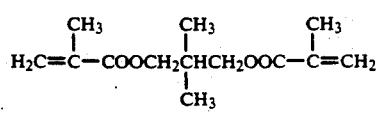

wherein n is an integer of 2 to 6 and $R^1$ is a methyl group or a hydrogen atom, -continued
wherein n is an integer of 1 to 20 and $R^1$ is a methyl group or a hydrogen atom,
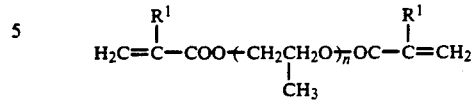
where n is an integer of 1 to 13 and $R^1$ is a methyl group or a hydrogen atom,
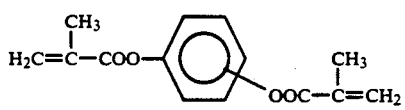
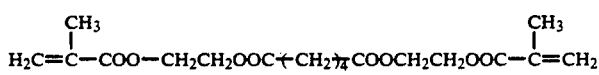
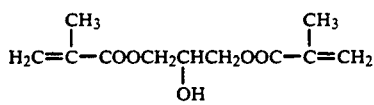
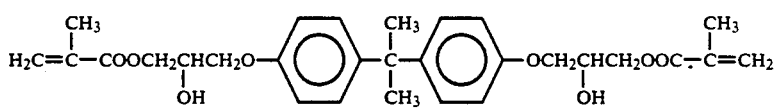
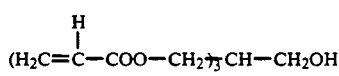
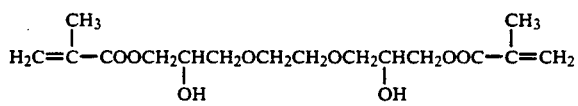
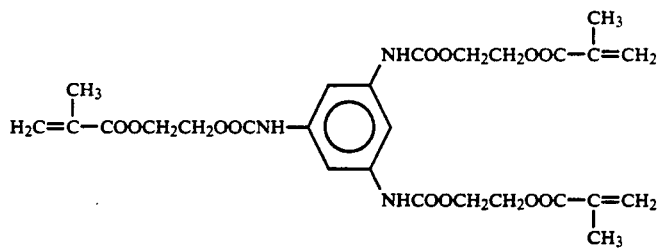
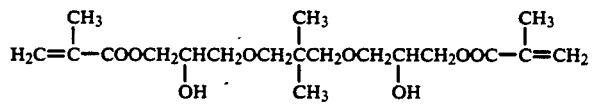

-continued

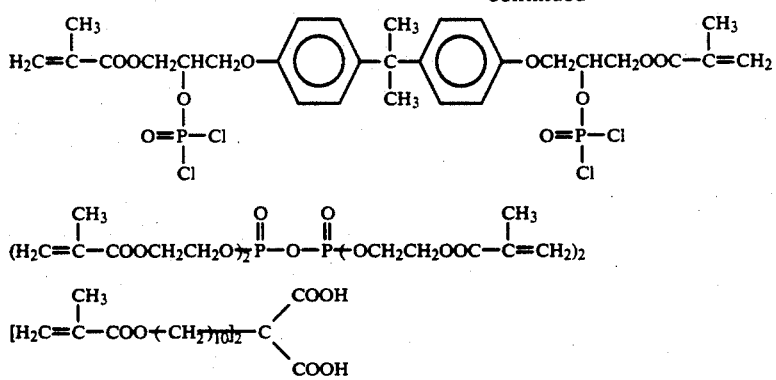

As the (meth)acrylate monomer used in the present invention, multifunctional (meth)acylates are preferred for the purpose of the providing the obtained dental restorative material with high mechanical strength, and monofunctional (meth)acrylates are generally not preferred. However, in some cases monofunctional (meth)acrylates may also be incorporated depending on the use and object of the restorative material to prepare, and, then, it is preferred that such monofunctional (meth)acrylate be incorporated in an amount not exceeding 35% by weight based on the weight of total (meth)acrylates. Such mixture of (meth)acrylates is referred to as "monomer composition" in this invention. Examples of the monofunctional (meth)acrylate are as follows.

methyl (meth)acrylate,
stearyl (meth)acrylate,
phenyl (meth)acrylate,
2-hydroxyethyl (meth)acrylate,
dimethylaminoethyl (meth)acrylate,
γ-methacryloyloxypropyltrimethoxysilane,
10-methacryloyloxydecyl dihydrogen phosphate and
4-[2-methacryloyloxyethyloxycarbonyl]phthalic acid.

The mixing ratio of the inorganic filler (a) having a particle size of 0.1 μm or less surface-treated with a silane coupling agent (I) with the monomer composition (b) varies depending on the use of the obtained dental restorative material, but it should be at least 100 parts by weight, more preferably at least 150 parts by weight of the filler (a) based on 100 parts by weight of the monomer composition (b).

The surface-treated inorganic filler having a particle size of 0.1 μm or less may also be used for a prepolymerized microfiller which is prepared by kneading the inorganic filler (a) with the monomer composition (b), curing the mixture and crushing the cured product.

The restorative material of the present invention comprising the inorganic filler (a) having a particle size of 0.1 μm or less and the monomer composition (b) may further incorporate a relatively coarse inorganic filler (c) having a particle size exceeding 0.1 μm and less than 100 μm. The incorporation of such coarser inorganic filler will further increase the hardness and Young's modulus of the polymerized product, which are close to those of enamel.

As the coarser inorganic filler, the same materials as the afore-mentioned inorganic fillers having a particle size of 0.1 μm or less can be used, and preferably used are glasses and/or minerals containing silica as a principal component. It is preferred that such coarser fillers be also surface-treated with a silane coupling agent represented by formula (I), γ-methacryloyloxypropyltrimethoxysilane, or the like. The filler (c) is incorporated in an amount of up to 10 times the total weight of the inorganic filler (a) and the monomer composition (b).

The restorative material of the present invention may further incorporate a prepolymerized microfiller (d). The term "prepolymerized microfiller" in the present invention refers to a filler of a composite structure comprising an inorganic ultrafine filler having a particle size of 0.5 μm or less and an organic polymer phase filled with said inorganic ultrafine filler. For the inorganic filler can be used the same materials as used for the inorganic filler (a) having a particle size of 0.1 μm or less used in the present invention. Suitable for the organic polymer phase are crosslinked polymers formed by polymerization of multifunctional (meth)acrylates. The inorganic filler is, generally after being surface-treated with any surface treating agent, which may be a coupling agent represented by formula (I), incorporated in a high density of at least 100 parts by weight to 100 parts by weight of an organic polymer. Prepolymerized microfillers (d) having a particle size of 1 to 100 μm are used in the present invention, and they are incorporated in an amount up to 10 times the total weight of the inorganic filler (a) and the monomer composition (b).

The restorative material of the present invention can be cured by polymerization into shaped articles by application of energy from outside such as heating at 100° C. or higher or irradiation of electron beam without any initiator but, it is preferable to polymerize the restorative material with an initiator contained therein.

There are no particular limitations to the polymerization initiators used in the present invention and any known initiators may be used, but the preferable initiator is selected in consideration of polymerizability of the monomer and the polymerization conditions. For example, where a (meth)acrylate is heated to undergo polymerization, preferred initiators are organic peroxides such as benzoyl peroxide (hereinafter referred to as BPO), di-t-butyl peroxide and cumene hydroperoxide, and other compounds such as 2,2'-azobisisobutyronitrile and 1,1'-azobis(cyclohexane-1-carbonitrile).

On the other hand where room temperature polymerization is conducted, preferably used are such redox initiators as benzoyl peroxide/dimethyl aniline, cumene hydroperoxide/dimethyl aniline, cumene hydroperoxide/thiourea, ascorbic acid/$Cu^{2+}$ salt, organic sulfinic acid (or salts thereof)/amine/peroxide; tributylborane, organic sulfinic acids and the like.

Further where photopolymerization is conducted by irradiation of visible light, such redox systems as α-diketone/tertiary amine, α-diketone/aldehyde and α-diketone/mercaptan. Examples of the α-diketone are camphorquinone, diacetyl, 2,3-pentanedione, benzyl, acenaphthenequinone, phenanthracene and the like; examples of the tertiary amine are N,N-dimethylaminoethyl methacrylate, ethyl N,N-dimethylaminobenzoate, Michler's ketone, and the like; examples of the aldehyde are citroneral, laurylaldhehyde, o-phthaldialdehyde, p-octyloxybenzaldehyde, and the like and examples of the mercaptan are 1-decanethiol, thiosalicylic acid, 2-mercaptobenzoxazol, 4-mercaptoacetophenone, and the like. Also used preferably are α-diketone/organic peroxide/reducing agent systems comprising the above-mentioned redox systems with an organic peroxide added thereto.

Where photopolymerization is conducted by irradiation of ultraviolet light, preferred initiators are, in addition to the above-mentioned initiators for photopolymerization using visible light, 2,4,6-trimethylbenzoyldiphenylphosphine oxide, benzoin methyl ether, benzyl dimethyl ketal, benzophenone, 2-methylthioxantone, diacetyl, benzyl, azobisisobutyronitrile, tetramethylthiurumdisulfide and the like.

These initiators are added to the restorative material in an amount of 0.01 to 10% by weight based on the weight of the monomer (b) used.

The dental restorative material of the present invention may, if necessary, further incorporate additives such as polymerization inhibitor, ultraviolet absorber, fluorescent agent and pigment.

The dental restorative material of the present invention may be formulated in various forms depending on the intended use. The followings are typical examples of them.

(i) One-package paste or liquid form

The filler, monomer, and initiator are mixed into a paste or liquid. The initiator is a photopolymerization initiator and/or an initiator for medium or high temperature polymerization.

(ii) Two-package paste or liquid form

The oxidizing agent and reducing agent of a redox initiator system capable of catalyzing room temperature polymerization are each separately admixed with either the filler or monomer to give two paste or liquid packages.

(iii) powder-liquid form

This form is composed of a powder which is a mixture of the above-mentioned reducing agent (or oxidizing agent) and a filler powder, and a solution (liquid) of the above-mentioned oxidizing agent (or reducing agent) in the monomer.

(iv) Shaped article

This is prepared by forming the composition of (i) through (iii) into a shaped article, followed by curing by polymerization. Typical example is artificial tooth.

The restorative materials of the present invention in the forms of (i) through (iii) are offered to dentists or dental technicians, the users form the materials into various shaped articles, and cure them by polymerization, so that they exhibit functions as dental materials.

In the dental restorative material of the present invention comprising (a) an inorganic filler having a particle size of 0.1 μm or less surface-treated with a silane coupling agent (I) and (b) a hydrophobic multifunctional (meth)acrylate, the ultrafine filler having a particle size of 0.1 μm or less can be filled in resin matrices in a much larger amount than conventional restorative materials. As a result, the high-density filling of the ultrafine filler realizes various desirable effects including improvements in mechanical strength, abrasion resistance, hardness and polishability.

The restorative material of the present invention has an excellent durability, so that it can maintain the high strength over a long period of time under wet conditions.

Furthermore, unexpectedly, the handling of the polymerizable composition in its paste form has greatly been improved. Thus, pastes comprising the restorative material of the present invention are neither sticky nor thready, and are improved in shape retention (i.e. a crown formed of the paste will maintain its shape for a long time).

In the restorative material of the present invention, problems encountered with conventional materials, such as shrinking at polymerization, thermal expansion, discoloring and water absorption of cured articles are minimized.

As described heretofore, the dental restorative material of the present invention has various desirable properties which materials of prior art have never achieved, and is hence used satisfactorily as composite resins for foreteeth and molars (e.g. restorative filling materials, prosthesis materials such as inlays and crowns, artificial teeth, etc.) and as abutment construction materials.

EXAMPLES

Other features of the invention will become apparent in the course of the following descriptions of exemplary embodiments which are given for illustration of the invention and are not intended to be limiting thereof. The definitions and measurement methods of various characteristics described in the Examples are collectively shown at the end of this specification.

Synthesis Example 1

(Synthesis of 8-methacryloyloxyoctyltrimethoxysilane)

A reaction vessel fitted with a stirrer was charged with 50 g of 7-octenyl methacrylate, 250 mg of hydroquinone monomethyl ether and 1.5 cc of 1% chloroplatinic acid hexahydrate solution in tetrahydrofuran, and the mixture was heated to 40° C. To the mixture was added gradually 42 g of trichlorosilane with stirring, while the temperature of the mixture was kept at 45° C. or below. After the addition, the mixture was heated to 60° C. and reaction was conducted at this temperature for 1 hour to obtain 8-methacryloyloxyoctyltrichlorosilane.

Next, 500 cc of methanol and 100 g of triethylamine were charged to a reaction vessel fitted with a stirrer and the mixture was cooled down to 0° C. The 8-methacryloyloxyoctyltrichlorosilane synthesized above was filled in a dropping funnel, which was then connected to the reaction vessel. While the solution in the vessel was vigorously stirred under an atmosphere of dry N$_2$ gas, the 8-methacrylspecification. oyloxyoctyltrichlorosilane was gradually added dropwise. After completion of the dropwise addition, the temperature was kept at 0° C. for 24 hours and then elevated to room temperature. The solvent of the reaction mixture was distilled off in vacuo, and a large volume of ethyl ether was added to the residue. After insoluble trimethylamine hydrochloride salt had been removed by filtration, ethyl ether was distilled off to obtain 78 g of crude 8-methacryloyloxyoctyltrimethoxysilane. Gas chromatography analysis revealed that the purity of the 8-methacryloyloxyoctyltrimethoxysilane was 87.5%. To the crude compound 1.0 g of anhydrous ferric trichloride was added and the mixture was subjected to fractional distillation. Collection of fractions at 143° to 144° C. (0.1 mmHg) yielded 52 g of 8-methacryloloxyoctyltrimethoxysilane of a purity of 97.0%.

A 10% solution of the compound in $CDCl_3$ was subjected to $^1H$-NMR spectroscopy to give the following results.

$\delta = 6.1$ and 5.5: ethylenic proton signals of methacryloyl group
$\delta = 4.5$: proton signal of methoxy group
$\delta = 1.9$: methyl proton signal of methacryloyl group
$\delta = 4.2$ to 4.0: signals of methylene protons adjacent to oxygen atom
$\delta = 0.8$ to 0.4: signal of methylene proton adjacent to silicon atom
$\delta = 1.9$ to 1.0: signals of other methylene protons The integrated intensities of the above signals were found to be identical with the calculated values of 8-methacryloyloxyoctyltrimethoxysilane. In the Infrared spectrogram of the compound, the absorption at around 3020 cm$^{-1}$ originating from the stretching vibration of the terminal vinyl group of 7-octenylmethacrylate had disappeared, and, instead, the absorption originating from the deformation vibration of Si—C and that originating from skeletal vibration of Si—O—C were observed at around 1180 cm$^{-1}$ and 1090 cm$^{-1}$ respectively. Accordingly, the obtained compound was identified as 8-methacryloyloxyoctyltrimethoxysilane.

Synthesis Example 2

(Synthesis of 11-methacryloyloxyundecyltrimethoxysilane)

Following the same procedure as in Synthesis Example 1, 86 g of a crude product of 11-methacryloyloxyundecyltrimethoxysilane was obtained from 60 g of 11-undecenyl methacrylate.

A solution was prepared by dissolving 50 g of the obtained crude 11-methacryloyloxyundecyltrimethoxysilane in 500 ml of methanol, and the solution was cooled with dry ice-ethyl ether to give precipitates of 11-methacryloyloxyundecyltrimethoxysilane. undecyltrimethoxysilane. Recrystallization by the above procedure was repeated to obtain 27 g of 11-methacryloyloxyundecyltrimethoxysilane of a purity of 97.5%.

A 10% solution of the compound in $CDCl_3$ was subjected to $^1H$-NMR spectroscopy to give the following results. $\delta = 6.1$ and 5.5: ethylenic proton signals of methacryloyl $\delta = 4.5$: proton signal of methoxy group
$\delta = 1.9$: methyl proton signal of methacryloyl group
$\delta = 4.2$ to 4.0: signals of methylene protons adjacent to oxygen atom
$\delta = 0.8$ to 0.4: signals of methylene protons adjacent to silicon atom
$\delta = 1.9$ to 1.0: signals of other methylene protons The integrated intensities of the above signals were found to be identical with the calculated values of 11-methacryloyloxyundecyltrimethoxysilane. In the infrared spectrogram of the compound, the absorption at around 3020 cm$^{-1}$ originating from the stretching vibration of the terminal vinyl group of 10-undecenyl methacrylate had disappeared, and, instead, the absorption originating from the deformation vibration of Si—C and that originating from skeletal vibration of Si—O—C were observed at around 1180 cm$^{-1}$ and 1090 cm$^{-1}$ respectively. Accordingly, the obtained compound was identified as 11-methacryloyloxyundecyltrimethoxysilane.

Synthesis Example 3

(Synthesis of 20-methacryloyloxyeicosyltrimethoxysilane)

Following the same procedure as in Synthesis Example 1, 108 g of a crude 20-methacryloyloxyeicosyltrimethoxysilane was obtained from 93 g of 19-eicosenyl methacrylate. The crude compound obtained was purified in the same manner as in Synthesis Example 2, and 50 g of the crude compound gave 23 g of 20-methacryloyloxyeicosyltrimethoxysilane of a purity of 96%.

$^1H$-NMR and IR spectrogram of the product obtained showed that it was 20-methacryloyloxyeicosyltrimethoxysilane.

EXAMPLE 1

A flask was charged with 50 g of silica powder having an average particle size of 0.04 μm (OX-50 ®, available from Nippon Aerosil Co.), 7.5 g of the 8-methacryloyloxyoctyltrimethoxysilane obtained in Synthesis Example 1 and 500 ml of toluene, and the mixture was refluxed for 2 hours under heating with vigorous stirring and then allowed to cool. Toluene was first distilled off in vacuo, and the residual mixture was dried in vacuo for 12 hours and then heated at 90° C. for 2 hours in vacuo to fully distill off toluene, to give a surface-treated filler.

A monomer composition was prepared by mixing together 35 parts by weight of 1,10-decanediol dimethacrylate, 65 parts by weight of an addition product of 1 mole of 2,2,4-trimethylhexamethylenediisocyanate and 2 moles of glycerine dimethacrylate (hereinafter referred to as "U-4TH") and 1 part by weight of benzoyl peroxide. A pasty polymerizable composition was prepared by kneading 100 parts of the monomer composition prepared above and 150 parts of the surface-treated filler obtained above, followed by deaeration in vacuo.

The paste consistency (load: 40 g) of the composition is shown in Table 1.

EXAMPLES 2 THROUGH 8 AND COMPARATIVE EXAMPLE 1

The procedure of Example 1 was followed using OX-50 ® surface-treated with silane coupling agents shown in Table 1 instead of 8-methacryloyloxyoctyltrimethoxysilane used in Example 1, and compositions similar to that of Example 1 were obtained. Their paste consistencies are shown in Table 1.

TABLE 1

| No. | Silane coupling agent | Paste consistency (mm) |
|---|---|---|
| Example 1 | $H_2C=\overset{\underset{\displaystyle CH_3}{\mid}}{C}-COO+CH_2)_8Si+OCH_3)_3$ | 20.3 |

TABLE 1-continued

| No. | Silane coupling agent | Paste consistency (mm) |
|---|---|---|
| Example 2 | $H_2C=\underset{CH_3}{C}-COO(CH_2)_{11}-Si(OCH_3)_3$ | 23.4 |
| Example 3 | $H_2C=\underset{CH_3}{C}-COO(CH_2)_{11}-\underset{CH_3}{Si}Cl_2$ | 24.0 |
| Example 4 | $H_2C=\underset{CH_3}{C}-COO(CH_2)_{11}-SiCl_3$ | 23.7 |
| Example 5 | $H_2C=\underset{CH_3}{C}-COO(CH_2)_{11}-\underset{\phi}{Si}[O(CH_2)_{15}CH_3]_2$ | 24.5 |
| Example 6 | $H_2C=\underset{CH_3}{C}-COO(CH_2)_{11}-Si(NCO)_3$ | 23.8 |
| Example 7 | $H_2C=\underset{H}{C}-COS(CH_2)_{11}-Si(OCH_3)_3$ | 23.0 |
| Example 8 | $H_2C=\underset{CH_3}{C}-COO(CH_2)_{20}-Si(OCH_3)_3$ | 26.2 |
| Comparative Example 1 | $H_2C=\underset{CH_3}{C}-COO(CH_2)_{3}Si(OCH_3)_3$ | 13.8 |

COMPARATIVE EXAMPLE 2

The procedure of Example 1 was followed using 1 g of the same silane coupling agent as in Example 1 instead of 7.5 g of the agent to obtain a surface-treated filler. All of the filler could not be incorporated into the monomer because of increase in viscosity.

EXAMPLES 9 THROUGH 17 AND COMPARATIVE EXAMPLES 3 THROUGH 8

Compositions were prepared by kneading 150 parts by weight of the same surface-treated inorganic filler as used in Example 2 and 100 parts of monomers shown in Table 2. The compositions obtained were evaluated for paste consistency (load: 40 g). The results are shown in Table 2, wherein and also in succeeding descriptions the monomers are coded as below.

MMA: methyl methacrylate
DD: 1,10-decanediol dimethacrylate

ME-HD: 1,6-bis(2-methacryloyloxyethoxy)hexane

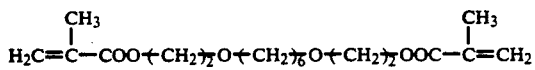

DTMA: ditetramethylene glycol dimethacrylate

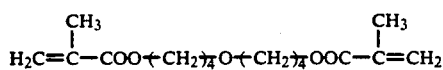

GDM-P: benzoic acid ester of glycerine dimethacrylate

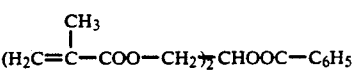

GDM: glycerine dimethacrylate
DHMPE: 1,2-bis(2-hydroxy-3-methacryloyloxypropoxy)ethane

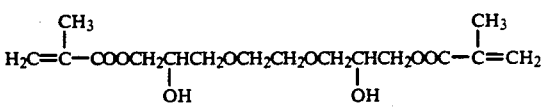

PETA: pentaerythritol triacrylate
NPG-HMP: 1,3-bis(2-hydroxy-3-methacryloyloxypropoxy)-2,2dimethylpropane

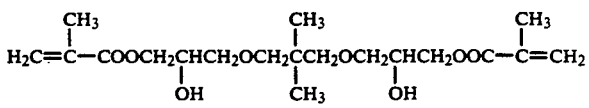

D-2.6E: 2,2-bis(methacryloyloxypolyethoxyphenyl)-propane (containing 2.6 ethoxy groups in a molecule on an average)
Bis-GMA: 2,2-bis[4-(3-methacryloyloxy-2-hydroxypropoxy)phenyl]propane
U-4TH: addition product of 1 mole of 2,2,4-trimethylhexamethylenediisocyanate and 2 moles of qlycerine dimethacrylate
3G: triethylene glycol dimethacrylate

TABLE 2

| No. | Monomer | Paste consistency (mm) |
|---|---|---|
| Example 9 | DD | 41.2 |
| Example 10 | ME-HD | 34.0 |
| Example 11 | DTMA | 36.1 |
| Example 12 | GDM-P | 32.5 |
| Comparative Example 3 | GDM | 18.7 |
| Comparative Example 4 | DHMPE | 15.5 |
| Comparative Example 5 | PETA | 18.2 |
| Comparative Example 6 | NPG-HMP | 14.0 |
| Example 13 | DD/Bis-GMA = 65/35 | 33.2 |
| Example 14 | DD/Bis-GMA = 50/50 | 26.7 |
| Comparative Example 7 | DD/Bis-GMA = 35/65 | 18.9 |
| Comparative Example 8 | DHMPE/D-2.6E = 65/35 | 16.1 |
| Example 15 | DHMPE/D-2.6E = 35/65 | 27.0 |
| Example 16 | DD/U-4TH = 50/50 | 31.2 |
| Example 17 | DD/D-2.6E = 50/50 | 32.3 |

It can be seen from Examples 9 through 12 and Comparative Examples 3 through 6 in Table 2 that hydrophobic multifunctional methacrylates as the monomer give the paste a high consistency value, which means a low viscosity, so that a large amount of the filler can be filled. Comparison of Examples 13 through 15 with Comparative Examples 7 and 8 shows that compsitions containing less than 50% by weight of the hydrophobic methacrylate monomer cause too high an increase in viscosity to incorporate a large amount of the filler.

EXAMPLE 18 AND COMPARATIVE EXAMPLE 9 for 15 hours to give a surface-treated filler. A polymerizable composition similar to that in Comparative Example 9 was prepared using the filler thus obtained, and evaluated in the same manner as in Comparative Example 9. The results are also shown in Table 3. The results show that no improvement in paste consistency of a composition was achieved by amine treatment.

COMPARATIVE EXAMPLE 11

Particulate silica having an average particle size of 1.8 μm and a particle size range of from 0.1 μm to 7 μm (hereinafter referred to as "filler FS") was obtained by pulverizing fused silica granules with a vibrating ball mill, followed by classification. Surface treatment was conducted on 100 parts by weight of the powder thus obtained with 2 parts by weight of 11-methacryloyloxyundecyltrimethoxysilane and 200 parts by weight of toluene in the same manner as in Example 1. A pasty composition was prepared by kneading 150 parts by weight of the surface-treated filler thus obtained and 100 parts of the monomer obtained in Example 1, and evaluated for paste consistency and compressive strength in the same manners in Example 1 and Example 18 respectively. The results are shown in Table 3.

EXAMPLE 19 AND COMPARATIVE EXAMPLES 12 THROUGH 14

Pasty compositions were prepared by kneading 150 parts by weight of the surface-treated inorganic fillers used in Example 18 and Comparative Example 11, and 100 parts by weight of monomers shown in Table 3 and containing 1% by weight of benzoyl peroxide, and evaluated for paste consistency an compressive strength in the same manners in Example 1 and Example 18 respectively. The results are shown in Table 3.

TABLE 3

| | Filler (average particle size) | Surface treating agent | Monomer composition | Compressive strength (kg/cm$^2$) | Paste consistency (mm) |
|---|---|---|---|---|---|
| Example 18 | OX-50 (0.04 μm) | 11-MUS[1] | U-4TH/DD = 65/35 | 4010 | 23.4 |
| Comparative Example 9 | " | γ-MPS[2] | " | 3580 | 13.8 |
| Comparative Example 10 | " | " | " | 3570 | 13.5 |
| Comparative Example 11 | FS (1.8 μm) | 11-MUS[1] | " | 2820 | at least 50 |
| Example 19 | OX-50 (0.04 μm) | " | U-4TH/MMA = 65/35 | 3660 | 27.8 |
| Comparative Example 12 | " | " | U-4TH/MMA = 35/65 | 2380 | 28.1 |
| Comparative Example 13 | " | " | MMA | 1530 | 33.5 |
| Comparative Example 14 | FS (1.8 μm) | " | " | 1310 | at least 50 |

[1] 11-methacryloyloxyundecyltrimethoxysilane
[2] γ-methacryloyloxypropyltrimethoxysilane The pasty polymerizable compositions obtained in Example 2 and Comparative Example 2 were polymerized by heating at 130° C. under a pressure of 1.5 atmosphere for 1 hour. The compressive strengths of the cured articles thus obtained are shown in Table 3.

COMPARATIVE EXAMPLE 10

A dispersion was prepared by dispersing 20 g of OX-50 ® (the filler has an acidity of surface site of +3.3 to +4.1) in 150 ml of ethanol. To the dispersion obtained 2.1 ml of n-propylamine was added and the mixture was stirred for 5 minutes at room temperature. Then, 3 g of γ-methacryloyloxypropyltrimethoxysilane was added, and the mixture was stirred for 20 minutes at room temperature. After ethanol had been distilled off using an evaporator, the resudue was dried at 80° C. in vacuo As is apparent from Table 3, the compositions of the present invention comprising an ultrafine filler treated with a silane coupling agent having a long-chain alkylene group and a multifunctional methacrylate have a large paste consistency value in their paste form and the cured articles therefrom are excellent in mechanical strength.

COMPARATIVE EXAMPLE 15

A polymerizable composition was prepared by kneading 50 parts by weight of the surface-treated inorganic filler and 100 parts by weight of the monomer both obtained in Example 2, and then cured by polymerization in the same manner as in Example 18. The article thus obtained showed a compressive strength of only 3,020 kg/cm². Comparison of this with Example 18 makes it clear that a filler contained in only a small amount leads to insufficient mechanical strength.

EXAMPLE 20

A polymerizable composition was prepared by kneading 300 parts by weight of the surface-treated inorganic filler obtained in Example 2 and 100 parts by weight of the monomer composition obtained in Example 1. The composition was heated at 130° C. under a pressure of 1.5 atmosphere for 1 hour to effect polymerization. The cured material was pulverized with a vibrating ball mill and the resulting powder was sieved to give an prepolymerized microfiller having an average particle size of 12 μm and a particle size range of 0.1 to 100 μm.

A monomer composition was prepared by mixing and dissolving 35 parts by weight of 1,10-decanediol dimethacrylate, 65 parts by weight of U-4TH and 0.5 part by weight of 2,4,6-trimethylbenzoyldiphenylphosphine oxide. A pasty composition was prepared by kneading 100 parts by weight of the thus prepared monomer composition, 400 parts by weight of the filler obtained above and 200 parts by weight of the inorganic filler obtained in Example 2. The paste obtained showed a paste consistency (load: 1 kg) of 24.2 mm. The paste was not sticky and had a good shape retention property, thus being an excellent dental restorative material with high operatability.

The paste was subjected to photoirradiation for 90 seconds by using a xenon lamp (Dentacolor XS ® available from Kulzer) to effect polymerization, and the product was further heated at 120° C. for 30 minutes to give a cured article. The cured article showed a compressive strength, flexural strength and Brinell hardness of 4,520 kg/cm², 1,020 kg/cm² and 48 respectively.

COMPARATIVE EXAMPLE 16

Using the same inorganic filler as used in Comparative Example 1, an attempt was made to prepare a prepolymerized microfiller with the same filler/monomer ratio as that in Example 20. However, since the viscosity was too high, it was not possible to knead all of the inorganic filler into the monomer.

EXAMPLE 21

An amount of borosilicate glass (Pyrex Glass, available from Dow Corning Co.) was sieved with a vibrating ball mill, and the powder was then classified to give particles having an average particle size of 2.4 μm and a particle size range of 0.1 to 20 μm. A dispersion containing 400 parts by weight of the thus obtained powder, 1,000 parts by weight of toluene and 10 parts by weight of 11-methacryloyloxyundecyltrimethoxysilane was refluxed under heating for 2 hours and then allowed to cool. The powder was recovered by vacuum filtration, dried in vacuo for 12 hours and then in air at 90° C. for 2 hours to give a surface-treated filler. A pasty polymerizable composition was obtained by kneading 650 parts by weight of the thus obtained filler, 200 parts by weight of the silica filler obtained in Example 2 and 100 parts of the monomer composition obtained in Example 20, followed by deaeration in vacuo. The paste was measured for paste consistency at a load of 1 kg. The paste was irradiated with a xenon lamp (Dentacolbr XS ® available from Kulzer) to undergo photopolymerization, and the obtained product was further cured by heating at 120° C. for 30 minutes. The cured product was evaluated in the same manner as in Example 20. The results are shown in Table 4.

COMPARATIVE EXAMPLE 17

The procedure of Example was followed using the silica filler obtained in Comparative Example 1, instead of the silica filler used in Example 21 to obtain a monomer composition having the same filler/monomer ratio as that in Example 21. All of said filler could not be incorporated into the monomer composition because of increase in viscosity.

COMPARATIVE EXAMPLE 18

There were kneaded 150 parts of the surface-treated ultrafine silica filler and 100 parts of the monomer composition of Comparative Example 1. To the mixture was gradually added and kneaded a borosilicate glass filler surface-treated with γ-methacryloyloxypropyltrimethoxysilane instead of the 11-methacryloyloxyundecyltrimethoxysilane used in Example 21 until the paste consistency reached about the same level as that in Example 21. 300 parts by weight of the glass filler could be kneaded. The results of evaluation on the thus obtained composition are also shown in Table 4.

EXAMPLE 22 AND COMPARATIVE EXAMPLES 19 AND 20

Compositions shown in Table 4 were prepared using the inorganic fillers of Example 21 and Comparative Examples 17 and 18, and evaluated in the same manner as above. The results are also shown in Table 4.

TABLE 4

|  | Example 21 | Example 22 | Comparative Example 18 | Comparative Example 19 | Comparative Example 20 |
|---|---|---|---|---|---|
| Polymerizable monomer | | | | | |
| Composition | U-4TH/DD = 65/35 | U-4TH/DD = 65/35 | U-4TH/DD = 65/35 | U-4TH/DD = 65/35 | U-4TH/DD = 65/35 |
| Parts by weight incorporated | 100 | 100 | 100 | 100 | 100 |
| Ultrafine filler | | | | | |
| Surface treating agent | 11-MUS[1] | 11-MUS | γ-MPS | γ-MPS | 11-MUS |
| Parts by weight incorporated | 200 | 150 | 150 | 150 | 50 |
| Glass filler | | | | | |
| Surface treating agent | 11-MUS | γ-MPS[2] | γ-MPS | 11-MUS | 11-MUS |
| Parts by weight incorporated | 350 | 450 | 300 | 380 | 500 |
| Paste consistency (mm) | 20.2 | 20.8 | 19.9 | 20.4 | 22.6 |
| Compressive strength (kg/cm²) | 5620 | 5230 | 3990 | 4530 | 4230 |
| Flexural strength (kg/cm²) | 1770 | 1530 | 1410 | 1440 | 1610 |

TABLE 4-continued

| | Example 21 | Example 22 | Comparative Example 18 | Comparative Example 19 | Comparative Example 20 |
|---|---|---|---|---|---|
| Brinell hardness | 92 | 81 | 66 | 68 | 73 |

(1) 11-methacryloyloxyundecyltrimethoxysilane
(2) γ-methacryloyloxypropyltrimethoxysilane

EXAMPLE 23

A mixture containing 50 parts by weight of an ultrafine γ-alumina having an average particle size of 0.02 μm (Aluminum Oxide C®, available from Nippon Aerosil Co), 10 parts by weight of 11-methacryloyloxyundecyltrimethoxysilane and 500 ml of toluene was refluxed for 2 hours under heating with vigorous stirring and then allowed to cool. Toluene was first distilled off in vacuo, and the residual mixture was dried in vacuo for 12 hours and then heated at 90° C. for 2 hours in vacuo to fully distill off toluene, to give a surface-treated ultrafine alumina filler. Next, an amount of lanthanum glass powder (GM 3168®, available from Shott) was pulverized and sieved to give a powder having an average particle size of 2.8 μm and a particle size range of 0.1 to 10 μm. Surface treatment was conducted on 100 parts by weight of the thus obtained powder with 2 parts by weight of 11-methacryloyloxyundecyltrimethoxysilane in the same manner as for the borosilicate glass in Example 21.

A monomer composition was prepared by mixing together 30 parts by weight of D-2.6E, 35 parts by weight of U-4TH, 35 parts by weight of DD and 0.5 part by weight of 2,4,6-trimethylbenzoyldiphenylphosphine oxide.

Using these fillers and monomer composition thus obtained, a polymerizable composition shown in Table 5 was prepared and evaluated in the same manner as in Example 21. The results are shown in Table 5.

COMPARATIVE EXAMPLE 21

Surface treatment was conducted on 50 parts by weight of the γ-alumina powder of Example 23 with 10 parts by weight of γ-methacryloyloxypropyltrimethoxysilane. This filler was then used to obtain a polymerizable composition of the same filler/monomer ratio as that in Example 23. However, all of the filler could not be kneaded into the monomer composition because of increase in viscosity.

COMPARATIVE EXAMPLE 22

A polymerizable composition with components and the filler/monomer ratio shown in Table 5 was prepared using the surface-treated alumina filler obtained in Comparative Example 21 and evaluated in the same manner as in Example 23. The results are also shown in Table 5.

TABLE 5

| | Example 23 | Comparative Example 22 |
|---|---|---|
| Monomer Composition | D-2.6E/U-4TH/DD = 30/35/35 | D-2.6E/U-4TH/DD = 30/35/35 |
| Parts by weight | 100 | 100 |
| Ultrafine filler | | |
| Surface treating agent | 11-MUS | γ-MPS |
| Parts by weight | 200 | 150 |
| Glass filler | | |
| Surface treating agent | 11-MUS | 11-MUS |
| Parts by weight | 800 | 350 |
| Paste consistency (mm) | 20.5 | 20.6 |
| Compressive strength (kg/cm²) | 5920 | 4820 |
| Flexural strength (kg/cm²) | 1680 | 1480 |
| Brinell hardness | 92 | 66 |

EXAMPLE 24

Test specimens for flexural strength were prepared by using the polymerizable composition obtained in Example 21 and by the same curing method as used in Example 21. The specimens were, for the purpose of accelerating deterioration, kept immersed in water at 70° C., and measured for flexural strength after one day, 10 days, 30 days and 100 days of immersion. The results are shown in Table 6.

COMPARATIVE EXAMPLE 23

A monomer composition was prepared by mixing and dissolving 65 parts by weight of Bis-GMA, 35 parts by weight of 3G and 0.5 part by weight of 2,4,6-trimethylbenzoyldiphenylphosphine oxide.

A polymerizable composition was prepared by kneading 100 parts by weight of the monomer composition obtained above, 150 parts by weight of the OX-50 surface-treated with γ-MPS and 300 parts by weight of borosilicate glass surface-treated with γ-MPS, the latter two having been obtained in Comparative Example 18. The composition was evaluated in the same manner as in Example 24. The results are shown in Table 6.

TABLE 6

| | Flexural strength (kg/cm²) | | | | |
|---|---|---|---|---|---|
| | | immersed in water at 70° C. for: | | | |
| | Initial | 1 day | 10 days | 30 days | 100 days |
| Example 24 | 1,770 | 1,680 | 1,670 | 1,640 | 1,620 |
| Comparative Example 23 | 1,450 | 1,330 | 1,280 | 1,150 | 1,020 |

It is clear from Table 6 that the restorative material of the present invention maintains its high strength over a long period of time in water at 70° C., and is thus excellent in water resistance.

In the Examples above, the definitions and measuring methods of various characteristics are as follows.

(i) Average particle size and particle size range

For the ultrafine powders with a paricle size of 0.1 μm or less, the particle size was determined based on transmission electron photomicrograph or by conversion from the specific surface area determined by BET method. For the fillers with a particle size exceeding 0.1 μm, a Horiba model CAPA 500 particle size autoanalyzer was used. The measurement was made with the centrifugal and gravitational sedimentation and light transmission technique.

(ii) Paste consistency

For the pasty compositions obtained by kneading a fixed amount of a monomer and a fixed amount of a surface-treated inorganic filler, it can be said that the lower the viscosity of the paste is, the larger the maximum incorporation amount of the filler will be.

In the Examples, the value measured in the following manner was defined as "consistency" and used as an index of the amount of the filler incorporated or to be incorporated in the monomer composition. 0.5 ml of the paste was weighed and allowed to stand in a constant temperature room at 25° C. for 24 hours. Then the paste was heaped in the middle of a glass plate (5×5 cm). Another glass plate (5×5 cm) was then gently placed thereon under a load of 40 g or 1 kg. After 120 seconds, the major axis and minor axie of the ovally spread paste body were measured through the upper glass plate. The arithmetic mean of both the values was taken as the consistency. The measurement was conducted at 25° C., and the consistency values shown in Tables are each the mean of the three independent measurements.

(iii) Flexural strength

A paste specimen was filled into a 2×2×30 mm mold and cured under prescribed conditions, and the cured article was then taken out of the mold. The thus obtained specimen was stored in water at 37° C. for 24 hours and then subjected to a three-point flexural test (span between terminal bearing edges=20 mm; cross head speed=1 mm/min) on an Instron Universal tester. The data shown in Tables are each the mean of 10 measurements (10 test specimens).

(iv) Compressive strength

A paste specimen was filled into a cylindrical mold, 4 mm in diameter and 4 mm in height, and cured by polymerization in a prescribed manner. The molded article was taken out of the mold, immersed in water at 37° C. for 24 hours and then tested on an Instron universal tester at a cross head speed of 2 mm/min. The values are each the mean of 10 specimens.

(v) Brinell hardness

A paste specimen was filled into a mold having a diameter of 10 mm and a thickness of 5 mm, a cover glass was brought into contact with the upper surface of the specimen under pressure, and curing by polymerization was conducted under prescribed conditions.

The cured specimen was taken out of the mold, and the face that had been kept in contact with the glass was polished with an abrasive paper with 220 grit to a depth of 0.5 mm and subjected to testing.

Obviously, numerous modifications and variations of the present invention are possible in light of the above teachings. It is therefore to be understood that within the scope of the appended claims, the invention may be practiced otherwise than as specifically described herein.

What is claimed is:

1. A dental restorative material comprising:
   (a) an ultrafine inorganic filler with a size of 0.1 μm or less which is insoluble in water and surface-treated with a silane coupling agent represented by the following general formula (I) in an amount of at least 3% by weight based on the weight of the filler:

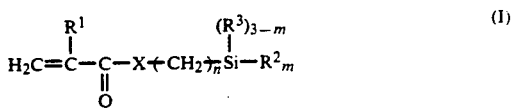

wherein $R^1$ is a hydrogen atom or a methyl group, $R^2$ is a hydrolyzable group, $R^3$ is a hydrocarbon group having 1 to 6 carbon atoms, X is an oxygen or sulfur atom, m is 2 or 3 and n is an integer of 8 to 20; and (b) a (meth)acrylate monomer composition containing at least 50% by weight based on the weight of the composition of at least one hydrophobic multifunctional (meth)acrylate represented by the following general formula (II)

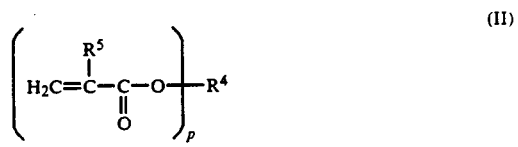

wherein $R^4$ is an organic group having 7 to 40 carbon atoms, composed of 1 to 8 hydrocarbon groups having 2 to 40 carbon atoms, at least one of said hydrocarbon groups having at least 4 carbon atoms, the ratio of the number of total carbon atoms, x, contained in the hydrocarbon groups to the number of the hydrocarbon groups, y, contained in said organic group satisfying: $x/y>3$; $R^5$ is a hydrogen atom or a methyl group and p is an integer of 2 to 8;

wherein said surface-treated inorganic filler is incorporated in an amount of at least 100 parts by weight based on 100 parts by weight of said monomer composition.

2. A dental restorative material according to claim 1, said material further comprising an inorganic filler having a particle size of 0.1 μm to 100 μm.

3. A dental restorative material according to claim 1, said material further comprising a prepolymerized microfiller having a particle size of 0.1 μm to 100 μm.

4. A dental restorative material according to claim 1, said material further comprising a polymerization initiator.

5. A dental restorative material according to claim 1, wherein said silane coupling agent is represented by the general formula (I) wherein $R^1$ is a methyl group, $R^2$ is an alkoxy group, X is an oxygen atom and m is an integer of 3.

6. A dental restorative material according to claim 1, wherein said inorganic filler is silica.

7. A dental restorative material according to claim 1, wherein said inorganic filler is alumina.

8. A dental restorative material according to claim 1, wherein said hydrophobic multifunctional (meth)acrylate is represented by the general formula (II) wherein $R^4$ is an organic group represented by the following general formula:

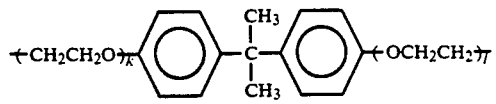

wherein k and l are integers satisfying $0 \leqq k+l \leqq 7$, and p is an integer of 2.

9. A dental restorative material according to claim 1, wherein said hydrophobic multifunctional (meth)acrylate is represented by the general formula (II) wherein $R^4$ is an organic group represented by the following general formula:

$$-(CH_2)_k-$$

wherein k is an integer of 7 to 20 and p is an integer of 2.

10. A dental restorative material according to claim 1, said material being a shaped article obtained by polymerization of said monomer composition.

* * * * *